United States Patent [19]

Forsyth et al.

[11] 3,978,060

[45] Aug. 31, 1976

[54] METHOD OF ERADICATING INTERNAL PARASITES

[75] Inventors: Bruce Adam Forsyth, Croydon; Richard Burridge Warner, Ringwood, both of Australia

[73] Assignee: ICI Australia Limited, Melbourne, Australia

[22] Filed: Sept. 27, 1974

[21] Appl. No.: 510,124

[30] Foreign Application Priority Data

Oct. 15, 1973 Australia............................. 5252/73
Nov. 13, 1973 Australia............................. 5637/73
Nov. 27, 1973 Australia............................. 5787/73

[52] U.S. Cl................................. 424/270; 424/321
[51] Int. Cl.²..................................... A61K 31/425
[58] Field of Search............................ 424/321, 270

[56] References Cited
UNITED STATES PATENTS 3,795,743 3/1974 Okuda et al. ...................... 424/321

OTHER PUBLICATIONS

*Chemical Abstracts*, (1962), 13666–13667, vol. 57.
*Chemical Abstracts*, (1974), vol. 80, 79151h.

*Primary Examiner*—Frederick E. Waddell
*Attorney, Agent, or Firm*—Cushman, Darby & Cushman

[57] ABSTRACT

A method of treating warm blooded animals to eradicate certain internal parasites; which method comprises administering to said warm blooded animals a therapeutic dose of a composition comprising as active ingredient a compound of formula I

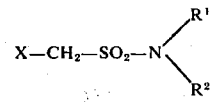

wherein X is halogen, and $R^1$ and $R^2$ which may be the same or different are selected from the group consisting of hydrogen, alkyl containing from 1 to 6 carbon atoms, — $NHR^3$ where $R^3$ is hydrogen or an alkyl group containing from 1 to 6 carbons atoms; and when either $R^1$ or $R^2$ is — $NHR^3$ then $R^2$ or $R^1$ respectively is hydrogen.

10 Claims, No Drawings

METHOD OF ERADICATING INTERNAL PARASITES

This invention relates to compositions for killing internal parasites of warm blooded animals; in particular it relates to compositions for killing trematodes or nematodes. An example of a trematode is the liver fluke (*Fasciola hepatica*) which is a parasite of bile ducts of the liver of ruminants, such as cattle, sheep and goats. The liver fluke each year causes a significant amount of economic loss, not only from the death of the host animal but also from the deterioration in the value of meat and wool produced by infected animals. In cattle a loss in milk yield from liver fluke infection will also occur and in addition the loss sustained by the condemnation of infected livers as human food may also be considerable.

An example of a nematode is *Haemonchus contortus* which is a nematode parasitic in the abomasum or fourth stomach of ruminants. It is a blood sucking parasite and when present in large numbers it can cause anaemia and finally the death of the host. It can cause extensive losses, not only in the value of the animals which it may kill but also in the diminished production of commercial items such as wool and meat. There is therefore a commercial need to treat animals with chemicals which are both safe and effective in reducing the incidence and severity of diseases caused by both trematodes and nematodes.

We have now found a class of compounds which are effective in killing liver fluke.

Accordingly we provide a method of treating warm blooded animals to eradicate certain internal parasites; which method comprises administering to said warm blooded animals a therapeutic dose of a composition comprising as active ingredient a compound of formula I

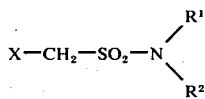

wherein X is halogen, and $R^1$ and $R^2$ which may be the same or different are selected from the group consisting of hydrogen, alkyl containing from 1 to 6 carbon atoms, $-NHR^3$ where $R^3$ is hydrogen or an alkyl group containing from 1 to 6 carbon atoms; and when either $R^1$ or $R^2$ is $-NHR^2$ then $R^2$ or $R^1$ respectively is hydrogen. Preferably X is fluorine, bromine or chlorine and $R^1$ and $R^2$ are hydrogen, or alkyl containing from 1 to 3 carbon atoms. Most preferably the compound of formula I is monochloromethane sulphonamide.

The process of the present invention has utility in the field of animal therapy. It is effective against both mature and immature liver fluke of the Fasciola genus. Many of the compositions also possess activity against nematodes such as *Haemonchus contortus*.

For effective treatment, certain dosage levels are desired depending upon the compound employed, the type of animal to be treated, and the particular helminth being combatted. In general, effective fluke efficacy is achieved when the composition is administered in a single dose at dosage levels of from about 25 to 200 mg active ingredient/kg of animal body weight, and preferably from about 50 to 100 mg active ingredient per kg of animal body weight.

The compositions of the present invention may be administered in a variety of ways, depending upon the particular animal employed, the type of anthelmintic treatment normally given to such an animal, the materials employed, and the particular helminths being combatted. It is preferred to administer them in a single efficacious oral or parenteral dose at a time when fluke or nematode infection is apparent or suspected. They may be employed alone or in combination with other anthelmintics, parasiticides or antibacterials.

The amounts of the active anthelmintic ingredient in the composition, as well as the remaining constituents are varied according to the type of treatment to be employed, the host animal, and the particular parasitic disease being treated. In general, however, compositions containing a total weight percent of the active compound or compounds ranging from 0.001 to 95% will be suitable with the remainder being any suitable carrier or vehicle. Furthermore, the compositions should contain enough of the active ingredient to provide an effective dosage for the proper treatment of the parasitic disease.

A number of modes of treatment may be employed, and each to some extent determines the general nature of the composition. For example, the anthelminthic compositions may be administered to domesticated animals in single unit oral dosage form such as a tablet, bolus, capsule or drench; in a liquid form suitable for parenteral administration; or they may be compounded as a feed premix to be ater admixed with the animal's food.

When the compositions are to be solid unit dosage forms as in tablets, capsules, or boluses, the ingredients other than the active ingredient may be any other pharmaceutically acceptable vehicles convenient in the preparation of such forms, and preferably materials nutritionally suitable such as starch, lactose, talc, magnesium stearate, vegetable gums, and the like. Moreover when capsules are employed, the active compound may be used in essentially undiluted form, the only extraneous material being that of the capsule casing itself which may be hard or soft gelatin or any other pharmaceutically acceptable encapsulating material. When the dosage form is to be used for parenteral administration, the active material is suitable admixed with an acceptable base vehicle. In all of such forms, i.e. in tablets, boluses, capsules, and injectable formulations, the active compound conveniently ranges from about 5 to 80% by weight of the total composition.

When the unit dosage form is to be in the form of a drench, the active ingredient may be mixed with agents which will aid in the subsequent suspending of the active compound in water, such as bentonite, clays, water-soluble starch, cellulose derivatives, gums, surface active agents and the like to form a dry predrench composition, and this predrench composition added to water just before use. In the predrench formulation, in addition to the suspending agent, such ingredients as preservatives, antiform compounds, and the like may be employed. Such a dry product may contain as much as 95% by weight of the active compound, the rest being contributed by the excipients. Preferably, the solid composition contains from 30% to 95% by weight of the active compound. Enough water should be added to the solid product to provide the proper dosage level within a convenient amount of liquid for a single oral dose. Liquid formulations containing up to 70 weight percent of dry ingredients will in general be suitable with the preferred range being from 5 to 50 weight percent.

Where the compositions are intended to be used as feeds, feed supplements, or feed premixes, they will be mixed with suitable ingredients of an animal's nutrient ration. The solid orally-ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone and the like are all suitable. The active compounds are intimately dispersed or admixed throughout the solid inert carrier by methods such as grinding, stirring, milling or tumbling. By selecting proper diluents and by altering the ratio of carrier to active ingredient, compositions of any desired concentration may be prepared. Feed supplement formulations containing from about 10 to 30% by weight of active ingredient are particularly suitable for addition to feeds. The active compound is normally dispersed or mixed uniformly in the diluent but in some instances may be adsorbed on the carrier.

These supplements are added to the finished animal feed in an amount adequate to give the final concentration of active ingredient desired for controlling or treating the helminth infection by way of the animal ration. Although the preferred level in feeds will depend on the particular compounds being employed, the active ingredients of this invention are normally fed at levels of 0.05–25% in the feed. As stated above, animals are preferably treated at a time when the infestation is apparent or suspected and the most preferred method for such treatment is via the single dose technique. Thus administration of medicated feed is not preferred but may certainly be employed. Similarly, the amounts of drug present in the feed may be reduced to levels in the order of 0.001% to 3.0 weight percent based on the weight of feed, and the medicated feed administered over prolonged periods. This would be in the nature of a preventive or propylactic measure but again is not the mode of choice. Another method of administering the compositions of this invention to animals whose feeds are conveniently pelleted, such as sheep, is to incorporate them directly in the pellets. For instance, the compositions are readily incorporated in nutritionally adequate alfalfa pellets at levels of 2 to 110 grams per pound of pellets for therapeutic use, and at lower levels for example 80 to 1000 milligrams per pound for prophylactic use, and such pellets fed to the animals.

Preferably the compositions are administered to the animal by parenteral dose and in a further aspect of our invention we provide an injectable composition comprising a sterile aqueous solution containing from 5 to 70% w/w preferably 5 to 50% w/w of the active ingredient.

The composition may be sterilized by methods known to those skilled in the art for the sterilization of injectable solution such as, for example, ultra filtration or gamma radiation.

The compositions may also optionally contain other drugs of veterinary utility. Veterinary drugs which may be present in the veterinary compositions of this invention, depending upon the mode of administration of the said compositions, include for example, piperazine, 1-diethyl-carbamyl-4-methyl-piperazine, tetrachloroethylene, organic and inorganic arsenical compounds, tetramisole, 2-phenyl-benzimidazole, thiabendazole, phenothiazine, mebendazole and pyrantel salts.

A particularly preferred composition according to our invention comprises an aqueous composition containing from 5 to 50% w/w of the active ingredient of formula I and from 0.1 to 25% w/w of L-tetramisole free base in the form of its acid salt, preferably the hydrochloride or phosphate salt. This composition is of use as a drench or, if sterilized, as an injectable solution for treatment of warm blooded animals infected with a wide variety of helminths.

The invention is now illustrated by, but by no means limited to, the following examples in which all parts are part by weight unless otherwise specified.

EXAMPLE 1

A 5% aqueous solution of monochloromethanesulphonamide was prepared. The activity of this solution against adult *Haemonchus contortus* was measured in the following way.

Three sheep which were known to be infected with *Haemonchus contortus* were dosed as shown in Table I with the solution. One was dosed by subcutaneous injection and two were dosed orally.

The effect on Haemonchus was measured initially by the change in the rate at which eggs appeared in the faeces. Samples of faeces were drawn before dosing and at days 7 and 10 after dosing. The samples were homogenised and diluted with water and the number of eggs per gram of faeces were assessed by standard procedure.

When the egg count showed a considerable reduction, the animal was slaughtered and the stomach was examined for worms.

The results are shown in Table I. The dose refers to the active ingredient, monochloromethanesulphonamide.

TABLE I

| Dose rate mg/kg | Route of Administration | Faecal Egg Count on Day shown | | | Worms present at P.M. |
|---|---|---|---|---|---|
| | | 0 | 7 | 10 | |
| 100 | Subcutaneous | 5,600 | 0 | 0 | 0 |
| 50 | Oral | 8,400 | 2,000 | 1,500 | Not killed |
| 100 | Oral | 40,000 | 0 | 0 | 0 |

EXAMPLE 2

The activity of a 5% aqueous solution of monochloromethanesulphonamide against adult *Fasciola hepatica* was measured in the following way.

Three sheep which were known to be infected with adult *Fasciola hepatica* were dosed as shown in Table II with the solution. One sheep was dosed by subcutaneous injection and two were dosed orally.

The effect on Fasciola was measured initially by the change in the rate at which eggs appeared in the faeces. Samples of faeces were drawn just before dosing and 4, 7 or 10 days after dosing. The samples were homogenised and diluted with water and the number of eggs per gram were assessed by standard procedures.

At the end of day 10, all sheep were slaughtered and the bile ducts were examined carefully for the presence of adult fluke.

The results are shown below in Table II. Dose rates refer to the active ingredient, monochloromethanesulphonamide.

TABLE II

| Dose rate mg/kg | Route Administration | Faecal Egg Count on Day shown | | | Worms present at P.M. |
|---|---|---|---|---|---|
| | | 0 | 4 | 7 | 10 | |
| 60 | Subcutaneous | 360 | 0 | — | — | 0 |
| 100 | Oral | 1,800 | — | 10 | — | 0 |
| 100 | Oral | 460 | — | 110 | 0 | — |

EXAMPLE 3

A 45% aqueous solution of monochloromethanesulphonamide was prepared. The activity of this solution against adult *Haemonchus contortus* was measured in the following way.

Nineteen sheep which were known to be infected with *Haemonchus contortus* were dosed as shown in Table III with the solution. Fifteen were dosed by subcutaneous injection and four were dosed orally.

The effect on Haemonchus was measured initially by the change in the rate at which eggs appeared in the faeces. Samples of faeces were drawn before dosing at at days 7 and 10 after dosing. The samples were homogenised and diluted with water and the number of eggs per gram of faeces were assessed by standard procedure.

When the egg count showed a considerable reduction, the animal was slaughtered and the stomach was examined for worms.

The results are shown in Table III. The dose refers to the active ingredient, monochloromethanesulphonamide.

TABLE III

| Dose rate mg/kg | Route * | Faecal egg count Day 0 | Day 7 | P.M. result | |
|---|---|---|---|---|---|
| 20 | S/C | 6,400 | 2,200 | Not killed | |
| 20 | S/C | 45,00 | 5,600 | " | |
| 20 | S/C | 15,000 | 11,400 | " | |
| 20 | S/C | 8,800 | 1,300 | " | |
| 40 | S/C | 9,000 | 1,400 | " | |
| 40 | S/C | 12,200 | 5,600 | 970 | *H. contortus* |
| 40 | S/C | 10,200 | 1,600 | 620 | " |
| 40 | S/C | 12,000 | 600 | 260 | " |
| 60 | S/C | 4,400 | 200 | 0 | " |
| 60 | S/C | 9,200 | 200 | 140 | " |
| 60 | S/C | 23,800 | 0 | 0 | " |
| 60 | S/C | 11,800 | 0 | 0 | " |
| 60 | S/C | 4,000 | 0 | 0 | " |
| 60 | S/C | 10,800 | 0 | 9 | " |
| 60 | Oral | 4,600 | 300 | 230 | " |
| 60 | Oral | 3,200 | 600 | 20 | " |
| 100 | S/C | 14,200 | 0 | 0 | " |
| 100 | Oral | 18,000 | 0 | 0 | " |
| 100 | Oral | 12,200 | 0 | 0 | " |

* S/C subcutaneous injection

EXAMPLE 4

The activity of a 45% aqueous solution of monochloromethanesulphonamide against adult *Fasciola hepatica* was measured in the following way.

Nine sheep which were known to be infected with adult *Fasciola hepatica* were dosed as shown in Table IV with the solution. Seven sheep were dosed by subcutaneous injection and two were dosed orally.

The effect on Fasciola was measured initially by the change in the rate at which eggs appeared in the faeces. Samples of faeces were drawn just before dosing and 4, 7 or 10 days after dosing. The samples were homogenised and diluted with water and the number of eggs per gram were assessed by standard procedures.

At the end of day 10, all sheep were slaughtered and the bile ducts were examined carefully for the presence of adult fluke.

The results are shown below in Table IV. Dose rates refer to the active ingredient, monochloromethanesulphonamide.

TABLE IV (Liver Fluke (adult worms))

| Dose rate mg/kg | Route * | Faecal Egg Count Day 0 | Day 10 | P.M. result |
|---|---|---|---|---|
| 100 | Oral | 1,800 | 0 | 0 fluke |
| 100 | Oral | 460 | 100 | 0 fluke |
| 75 | S/C | 280 | 0 | 0 fluke |
| 75 | S/C | 350 | 0 | 0 fluke |
| 60 | S/C | 360 | 50 | 0 fluke |
| 50 | S/C | 470 | 40 | 69 fluke |
| 50 | S/C | 30 | 0 | 14 fluke |
| 25 | S/C | 70 | 120 | Not killed |
| 25 | S/C | 280 | 520 | Not killed |

* S/C subcutaneous injection

EXAMPLE 5

The activity of a 45% aqueous solution of monochloromethanesulphonamide against immature forms of *Fasciola hepatica* of various ages was measured in the following way:

Each animal in a group of fluke-free sheep was infected with a similar volume of a suspension of metacercariae containing from 200 to 500 metacercariae. The animals were divided into several groups each containing 6 sheep — some were untreated (control group) and others were treated with various doses of the test chemical at different times after infection. In this way the age of the fluke at the time of dosing could be established.

After treatment the infection was allowed to develop to maturity (at least 11 weeks from infection); the animals were then killed and all the fluke in the liver were collected and counted. The average number of fluke surviving the treatment in each group of animals was compared with the average number in the control group. In this way the degree of control was calculated (expressed as a percentage kill).

The results are summarized in Table V.

TABLE V

| Age of fluke (weeks) | Dose (mg/kg) | % kill |
|---|---|---|
| 2 | 100 | 100 |
| 3 | 100 | 86 |
| 6 | 75 | 28 |
| 6 | 100 | 49 |
| 6 | 150 | 93 |

EXAMPLE 6

An aqueous solution containing 45% w/w monochloromethane sulphonamide and 6.8% w/w levamisole free base in the form of the hydrochloride salt was prepared. The solution was sterilized by filtration through a biological filter.

A steer of approximately 200 kg bodyweight was dosed by subcutaneous injection with 45 mls of the sterilized solution. On inspection 24 hours after injection only minor tissue reaction was observed at the injection site.

EXAMPLE 7

A 500 lb cow infested with Fasciola was dosed at 100 mg/kg of monochloromethanesulphonamide and 8 mg/kg levamisole hydrochloride with the following sterilized solution.

| | |
|---|---|
| Cl—CH$_2$—SO$_2$NH$_2$ | 45 % w/v |
| Levamisole HCl | 3.6% w/v |
| NaH$_2$PO$_4$ 2 H$_2$O | 2.0% w/v |
| Citric Acid | 2.4% w/v |
| Water to 100 vols | |

The dose was 10 ml of the above solution/100 lb bodyweight. This was given as 2 × 25 ml doses over the rib area.

Palpation of the injection sites for up to 14 days post treatment revealed only minor subcutaneous thickening and no observable lump or swelling. On post mortem examination 24 days post injection some yellow discolouration of the subcutaneous tissue over the subcutaneous muscle was apparent but this did not penetrate the muscle. There was no necrosis, fibrosis or oedema and after the carcass had cooled down the discolouration was barely recognizable.

There were no liver fluke found on post mortem.

EXAMPLE 8

A mixture was prepared consisting of

| | |
|---|---|
| Cl—CH$_2$—SO$_2$NH$_2$ | 45% w/v |
| Levamisole phosphate | equivalent 3.6% w/v of levamisole HCl |
| NaH$_2$ PO$_4$ 2 H$_2$O | 2.0% w/v |
| Citric Acid | 2.4% w/v |
| Water to 100 | |

The solution was sterilized by filtration.

Two cows weighing between 1000 and 1100 lbs infested with Fasciola were injected with 60 mls of the sterilized mixture in the middle of the left side over the last two ribs. The animals were slaughtered after 28 days and after skinning only a very faint blemish was observed at the injection site. No liver fluke were found on post mortem.

In parallel with the above two further cows weighing between 1000 and 1100 lbs were similarly injected with 37.5 mls of the solution. Similar results were obtained on post mortem.

EXAMPLE 9

A series of sulphonamides were tested for flukicidal activity in the following manner.

An aqueous solution of the test compound was sterilized by filtration and used as either a subcutaneous injection or an oral drench to dose sheep known to be infected with adult Fasciola hepatica. The effect on Fasciola was measured by the method of Example 2. The results are shown below in Table VI.

TABLE VI

| Dose rate mg/kg bodyweight and mode of administration | Test Compound | Faecal egg count on days shown | | | | | Worms present at P.M. |
|---|---|---|---|---|---|---|---|
| | | 0 | 4 | 7 | 10 | 15 | |
| 70 oral | I—CH$_2$—SO$_2$NH$_2$ | 450 | — | 30 | — | | — |
| 50 S/C | Br—CH$_2$—SO$_2$—NHEt | 260 | — | 180 | — | 0 | 0 |
| 50 S/C | Br—CH$_2$—SO$_2$NH$_2$ | 230 | 240 | 0 | 0 | | 0 |
| 50 S/C | Cl—CH$_2$—SO$_2$NHEt | 760 | — | 0 | 0 | | 0 |
| 40 oral | Cl—CH$_2$—SO$_2$N(Et)$_2$ | 130 | — | 0 | — | | 0 |
| 50 oral | F CH$_2$SO$_2$NH$_2$ (in admixture with FCl CH SO$_2$ NH$_2$) | 265 | — | 245 | — | 0 | — |

We claim:

1. A method for treating warm blooded animals to eradicate Fasciola sp and Haemonchus contortus; which method comprises administering internally to said warm blooded animals an effective amount of a composition comprising as active ingredient a compound of formula I

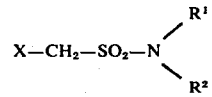

wherein X is halogen, and R$^1$ and R$^2$ which may be the same or different are selected from the group consisting of hydrogen and alkyl of from 1 to 6 carbon atoms.

2. The method of claim 1 wherein X is fluorine, bromine or chlorine.

3. The method of claim 1 wherein R$^1$ and R$^2$ which may be the same or different are hydrogen or alkyl containing 1 to 3 carbon atoms.

4. The method of claim 1 wherein the active ingredient is monochloromethanesulphonamide.

5. The method claim 1 wherein the composition is administered in a single dose at dosage levels of from about 25 to 200 mg active ingredient/kg of animal body weight.

6. The method of claim 5 wherein the single dose is at dosage levels of from 50 to 100 mg active ingredient per kg of animal body weight.

7. The method of claim 1 wherein said composition is a sterile aqueous solution containing from 5 to 70% w/w of the active ingredient and said composition is administered by injection.

8. The method of claim 7 wherein the composition comprises from 5 to 50% w/w of active ingredient.

9. The method of claim 7 wherein the composition comprises from 5 to 50% w/w of active ingredient, and from 0.1 to 25% w/w of L-tetramisole free base in the form of its acid salt.

10. The method of claim 7 wherein the composition comprises from 5 to 50% w/w of monochloromethane sulphonamide and from 0.1 to 25% w/w of L-tetramisole hydrochloride or phosphate.

* * * * *